(12) United States Patent
Griffin et al.

(10) Patent No.: US 9,433,762 B2
(45) Date of Patent: *Sep. 6, 2016

(54) CATHETER INCLUDING A COMPLIANT BALLOON

(71) Applicant: Boston Scientific Scimed, Inc., Maple Grove, MN (US)

(72) Inventors: Stephen Griffin, San Jose, CA (US); Huey Quoc Chan, San Jose, CA (US); Elaine Lim, Fremont, CA (US); Nhan Hue To, San Jose, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 177 days.

This patent is subject to a terminal disclaimer.

(21) Appl. No.: 14/034,025

(22) Filed: Sep. 23, 2013

(65) Prior Publication Data

US 2014/0012195 A1    Jan. 9, 2014

Related U.S. Application Data

(63) Continuation of application No. 13/233,692, filed on Sep. 15, 2011, now Pat. No. 8,540,668, which is a continuation of application No. 12/631,909, filed on Dec. 7, 2009, now Pat. No. 8,021,329, which is a continuation of application No. 11/008,452, filed on Dec. 9, 2004, now Pat. No. 7,632,242.

(51) Int. Cl.
| | |
|---|---|
| *A61M 25/10* | (2013.01) |
| *A61B 17/22* | (2006.01) |
| *A61M 25/00* | (2006.01) |
| *A61M 25/01* | (2006.01) |

(52) U.S. Cl.
CPC .... *A61M 25/1002* (2013.01); *A61B 17/22032* (2013.01); *A61M 25/0054* (2013.01); *A61M 25/10* (2013.01); *A61M 25/0105* (2013.01)

(58) Field of Classification Search
CPC .............. A61M 25/0054; A61M 25/0105; A61M 25/10; A61M 25/0013; A61M 25/0015; A61M 25/0138
See application file for complete search history.

(56) References Cited

U.S. PATENT DOCUMENTS

| | | | |
|---|---|---|---|
| 2,441,166 | A | 5/1948 | Raspet |
| 3,452,742 | A | 7/1969 | Muller |
| 3,625,200 | A | 12/1971 | Muller |
| 3,890,977 | A | 6/1975 | Wilson et al. |

(Continued)

FOREIGN PATENT DOCUMENTS

| | | | |
|---|---|---|---|
| AU | 723040 B2 | 8/2000 | |
| AU | 733966 B2 | 5/2001 | |

(Continued)

OTHER PUBLICATIONS

Helical Compression Springs, "Mechanical Design and Systems Handbook", H.A. Rothbart, 1964, p. 33-13 (one sheet).

*Primary Examiner* — Quynh-Nhu H Vu

(74) *Attorney, Agent, or Firm* — Seager, Tufte & Wickhem, LLP

(57) ABSTRACT

A catheter having an elongate shaft including a plurality of apertures disposed along at least a length of the shaft to facilitate bending. The catheter includes an inflatable balloon, wherein a subset of the plurality of apertures provides fluid communication from an inflation lumen to the inflatable balloon.

20 Claims, 6 Drawing Sheets

(56) References Cited

U.S. PATENT DOCUMENTS

| | | |
|---|---|---|
| 4,003,369 A | 1/1977 | Heilman et al. |
| 4,020,829 A | 5/1977 | Willson et al. |
| 4,215,703 A | 8/1980 | Willson |
| 4,327,736 A | 5/1982 | Inoue |
| 4,425,919 A | 1/1984 | Alston et al. |
| 4,545,390 A | 10/1985 | Leary |
| 4,547,193 A | 10/1985 | Rydell |
| 4,563,181 A | 1/1986 | Wijayarathna et al. |
| 4,637,396 A | 1/1987 | Cook |
| 4,665,906 A | 5/1987 | Jervis et al. |
| 4,690,672 A | 9/1987 | Veltrup |
| 4,717,379 A | 1/1988 | Ekholmer et al. |
| 4,721,117 A | 1/1988 | Mar et al. |
| 4,763,647 A | 8/1988 | Gambale |
| 4,781,186 A | 11/1988 | Simpson et al. |
| 4,796,629 A | 1/1989 | Grayzel et al. |
| 4,800,890 A | 1/1989 | Cramer |
| 4,811,743 A | 3/1989 | Stevens |
| 4,827,941 A | 5/1989 | Taylor et al. |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,921,476 A | 5/1990 | Wuchinich |
| 4,932,959 A | 6/1990 | Horzewski et al. |
| 4,934,380 A | 6/1990 | De Toledo et al. |
| 4,953,553 A | 9/1990 | Tremulis |
| 4,955,384 A | 9/1990 | Taylor et al. |
| 4,955,862 A | 9/1990 | Sepetka et al. |
| 4,964,409 A | 10/1990 | Tremulis |
| 4,966,163 A | 10/1990 | Kraus et al. |
| 4,989,608 A | 2/1991 | Ratner |
| 4,994,033 A | 2/1991 | Shockey et al. |
| 4,994,069 A | 2/1991 | Ritchart et al. |
| 4,998,923 A | 3/1991 | Samson et al. |
| 5,007,434 A | 4/1991 | Doyle et al. |
| 5,011,488 A | 4/1991 | Ginsburg et al. |
| 5,037,431 A | 8/1991 | Summers et al. |
| 5,037,609 A | 8/1991 | Nakonechny |
| 5,040,543 A | 8/1991 | Badera et al. |
| 5,049,132 A | 9/1991 | Shaffer et al. |
| 5,052,404 A | 10/1991 | Hodgson |
| 5,063,935 A | 11/1991 | Gambale |
| 5,084,013 A | 1/1992 | Takase |
| 5,087,244 A | 2/1992 | Wolinsky et al. |
| 5,095,915 A | 3/1992 | Engelson et al. |
| 5,106,455 A | 4/1992 | Jacobsen et al. |
| 5,125,395 A | 6/1992 | Adair |
| 5,141,518 A | 8/1992 | Hess et al. |
| 5,144,959 A | 9/1992 | Gambale et al. |
| 5,147,317 A | 9/1992 | Shank et al. |
| 5,181,668 A | 1/1993 | Tsuji et al. |
| 5,205,830 A | 4/1993 | Dassa et al. |
| 5,211,183 A | 5/1993 | Wilson |
| 5,213,576 A | 5/1993 | Abiuso et al. |
| 5,228,441 A | 7/1993 | Lundquist |
| 5,232,444 A | 8/1993 | Just et al. |
| 5,238,004 A | 8/1993 | Sahatjian et al. |
| 5,242,394 A | 9/1993 | Tremulis |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz et al. |
| 5,256,143 A | 10/1993 | Miller et al. |
| 5,256,144 A | 10/1993 | Kraus et al. |
| 5,259,393 A | 11/1993 | Corso et al. |
| 5,267,979 A | 12/1993 | Appling et al. |
| 5,300,032 A | 4/1994 | Hibbs et al. |
| 5,304,131 A | 4/1994 | Paskar et al. |
| 5,306,252 A | 4/1994 | Yutori et al. |
| 5,315,996 A | 5/1994 | Lundquist |
| 5,318,518 A | 6/1994 | Plechinger et al. |
| 5,322,064 A | 6/1994 | Lundquist |
| 5,329,923 A | 7/1994 | Lundquist |
| 5,330,429 A | 7/1994 | Noguchi et al. |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,365,942 A | 11/1994 | Shank et al. |
| 5,365,943 A | 11/1994 | Jansen |
| 5,368,564 A | 11/1994 | Savage |
| 5,370,609 A | 12/1994 | Drasler et al. |
| 5,376,084 A | 12/1994 | Bacich et al. |
| 5,406,960 A | 4/1995 | Corso |
| 5,411,476 A | 5/1995 | Abrams et al. |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,460,187 A | 10/1995 | Daigle et al. |
| 5,477,856 A | 12/1995 | Lundquist |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,527,292 A | 6/1996 | Adams et al. |
| 5,538,504 A | 7/1996 | Linden et al. |
| 5,538,512 A | 7/1996 | Zenzon et al. |
| 5,551,444 A | 9/1996 | Finlayson |
| 5,554,119 A | 9/1996 | Harrison et al. |
| 5,554,139 A | 9/1996 | Okajima et al. |
| 5,558,642 A | 9/1996 | Schweich, Jr. et al. |
| 5,562,619 A | 10/1996 | Mirarchi et al. |
| 5,569,197 A | 10/1996 | Helmus et al. |
| 5,569,218 A | 10/1996 | Berg et al. |
| 5,571,073 A | 11/1996 | Castillo et al. |
| 5,573,520 A | 11/1996 | Schwartz et al. |
| 5,584,821 A | 12/1996 | Hobbs et al. |
| 5,599,492 A | 2/1997 | Engelson et al. |
| 5,601,539 A | 2/1997 | Corso et al. |
| 5,605,162 A | 2/1997 | Mirzaee et al. |
| 5,605,543 A * | 2/1997 | Swanson .................. 604/102.02 |
| 5,611,775 A | 3/1997 | Machold et al. |
| 5,622,184 A | 4/1997 | Ashby et al. |
| 5,637,089 A | 6/1997 | Abrams et al. |
| 5,666,968 A | 9/1997 | Imran et al. |
| 5,666,969 A | 9/1997 | Urick et al. |
| 5,676,659 A | 10/1997 | McGurk et al. |
| 5,682,894 A | 11/1997 | Orr et al. |
| 5,688,234 A | 11/1997 | Frisbie |
| 5,690,120 A | 11/1997 | Jacobsen et al. |
| 5,720,300 A | 2/1998 | Fagan et al. |
| 5,722,609 A | 3/1998 | Murakami |
| 5,728,063 A | 3/1998 | Preissman et al. |
| 5,741,429 A | 4/1998 | Donadio et al. |
| 5,746,701 A | 5/1998 | Noone |
| 5,749,858 A | 5/1998 | Cramer et al. |
| 5,766,201 A | 6/1998 | Ravenscroft et al. |
| 5,769,830 A | 6/1998 | Parker et al. |
| 5,772,609 A | 6/1998 | Nguyen et al. |
| 5,788,654 A | 8/1998 | Schwager |
| 5,792,124 A | 8/1998 | Horrigan et al. |
| 5,795,331 A | 8/1998 | Cragg et al. |
| 5,797,856 A | 8/1998 | Frisbie et al. |
| 5,800,454 A | 9/1998 | Jacobsen et al. |
| 5,807,249 A | 9/1998 | Qin et al. |
| 5,827,225 A | 10/1998 | Ma Schwab |
| 5,827,229 A | 10/1998 | Auth et al. |
| 5,827,242 A | 10/1998 | Follmer et al. |
| 5,833,632 A | 11/1998 | Jacobsen et al. |
| 5,833,650 A | 11/1998 | Imran |
| 5,833,658 A | 11/1998 | Levy et al. |

(56) References Cited

U.S. PATENT DOCUMENTS

| | | | |
|---|---|---|---|
| 5,836,926 | A | 11/1998 | Peterson et al. |
| 5,843,033 | A | 12/1998 | Ropiak et al. |
| 5,843,050 | A | 12/1998 | Jones et al. |
| 5,843,051 | A | 12/1998 | Adams et al. |
| 5,843,244 | A | 12/1998 | Pelton et al. |
| 5,851,203 | A | 12/1998 | van Muiden |
| 5,866,561 | A | 2/1999 | Ungs et al. |
| 5,879,361 | A | 3/1999 | Nash et al. |
| 5,891,111 | A | 4/1999 | Ismael |
| 5,897,537 | A | 4/1999 | Berg et al. |
| 5,902,254 | A | 5/1999 | Magram |
| 5,904,657 | A | 5/1999 | Unsworth et al. |
| 5,906,618 | A | 5/1999 | Larson et al. |
| 5,911,715 | A | 6/1999 | Berg et al. |
| 5,911,717 | A | 6/1999 | Jacobsen et al. |
| 5,916,178 | A | 6/1999 | Noone et al. |
| 5,916,192 | A | 6/1999 | Nita et al. |
| 5,916,194 | A | 6/1999 | Jacobsen et al. |
| 5,919,163 | A | 7/1999 | Glickman |
| 5,931,830 | A | 8/1999 | Jacobsen et al. |
| 5,935,108 | A | 8/1999 | Katoh et al. |
| 5,947,985 | A | 9/1999 | Imran et al. |
| 5,951,458 | A | 9/1999 | Hastings et al. |
| 5,971,975 | A | 10/1999 | Mills et al. |
| 5,980,532 | A | 11/1999 | Wang et al. |
| 5,989,271 | A | 11/1999 | Bonnette et al. |
| 6,001,068 | A | 12/1999 | Uchino et al. |
| 6,004,279 | A | 12/1999 | Crowley et al. |
| 6,014,919 | A | 1/2000 | Jacobsen et al. |
| 6,017,319 | A | 1/2000 | Jacobsen et al. |
| 6,017,323 | A * | 1/2000 | Chee ................ 604/96.01 |
| 6,022,336 | A | 2/2000 | Zadno et al. |
| 6,022,369 | A | 2/2000 | Jacobsen et al. |
| 6,045,547 | A | 4/2000 | Ren et al. |
| 6,048,339 | A | 4/2000 | Zirps et al. |
| 6,059,809 | A | 5/2000 | Amor et al. |
| 6,063,101 | A | 5/2000 | Jacobsen et al. |
| 6,063,200 | A | 5/2000 | Jacobsen et al. |
| 6,066,361 | A | 5/2000 | Jacobsen et al. |
| 6,102,929 | A | 8/2000 | Conway et al. |
| 6,106,485 | A | 8/2000 | McMahon |
| 6,106,488 | A | 8/2000 | Fleming et al. |
| 6,120,477 | A | 9/2000 | Campbell et al. |
| 6,120,523 | A | 9/2000 | Crocker et al. |
| 6,139,510 | A | 10/2000 | Palermo et al. |
| 6,149,641 | A | 11/2000 | Ungs et al. |
| 6,165,292 | A | 12/2000 | Abrams et al. |
| 6,171,296 | B1 | 1/2001 | Chow |
| 6,183,410 | B1 | 2/2001 | Jacobsen et al. |
| 6,186,978 | B1 | 2/2001 | Samson et al. |
| 6,214,042 | B1 | 4/2001 | Jacobsen et al. |
| 6,217,567 | B1 | 4/2001 | Zadno-Azizi et al. |
| 6,231,543 | B1 | 5/2001 | Hegde et al. |
| 6,231,588 | B1 | 5/2001 | Zadno-Azizi |
| 6,234,995 | B1 | 5/2001 | Peacock, III |
| 6,251,092 | B1 | 6/2001 | Qin et al. |
| 6,260,458 | B1 | 7/2001 | Jacobsen et al. |
| 6,280,411 | B1 | 8/2001 | Lennox |
| 6,287,320 | B1 | 9/2001 | Slepian |
| 6,290,656 | B1 | 9/2001 | Boyle et al. |
| 6,296,616 | B1 | 10/2001 | McMahon |
| 6,296,631 | B2 | 10/2001 | Chow |
| 6,302,870 | B1 | 10/2001 | Jacobsen et al. |
| 6,315,757 | B1 | 11/2001 | Chee et al. |
| 6,325,790 | B1 | 12/2001 | Trotta |
| 6,338,725 | B1 | 1/2002 | Hermann et al. |
| 6,346,091 | B1 | 2/2002 | Jacobsen et al. |
| 6,352,515 | B1 | 3/2002 | Anderson et al. |
| 6,355,027 | B1 | 3/2002 | Le et al. |
| 6,368,315 | B1 | 4/2002 | Gillis et al. |
| 6,368,316 | B1 | 4/2002 | Jansen et al. |
| 6,379,369 | B1 | 4/2002 | Abrams et al. |
| 6,390,993 | B1 | 5/2002 | Cornish et al. |
| 6,398,758 | B1 | 6/2002 | Jacobsen et al. |
| 6,428,489 | B1 | 8/2002 | Jacobsen et al. |
| 6,431,039 | B1 | 8/2002 | Jacobsen et al. |
| 6,440,088 | B1 | 8/2002 | Jacobsen et al. |
| 6,478,778 | B1 | 11/2002 | Jacobsen et al. |
| 6,491,648 | B1 | 12/2002 | Cornish et al. |
| 6,491,671 | B1 | 12/2002 | Larson, III et al. |
| 6,508,803 | B1 | 1/2003 | Horikawa et al. |
| 6,511,503 | B1 | 1/2003 | Burkett et al. |
| 6,524,301 | B1 | 2/2003 | Wilson et al. |
| 6,530,934 | B1 | 3/2003 | Jacobsen et al. |
| 6,553,880 | B2 | 4/2003 | Jacobsen et al. |
| 6,579,246 | B2 | 6/2003 | Jacobsen et al. |
| 6,602,280 | B2 | 8/2003 | Chobotov |
| 6,610,046 | B1 | 8/2003 | Usami et al. |
| 6,623,452 | B2 | 9/2003 | Chien et al. |
| 6,638,245 | B2 | 10/2003 | Miller et al. |
| 6,648,854 | B1 | 11/2003 | Patterson et al. |
| 6,652,508 | B2 | 11/2003 | Griffin et al. |
| 6,766,720 | B1 | 7/2004 | Jacobsen et al. |
| 7,632,242 | B2 * | 12/2009 | Griffin et al. ............... 604/96.01 |
| 8,021,329 | B2 * | 9/2011 | Griffin et al. ............... 604/96.01 |
| 8,540,668 | B2 | 9/2013 | Griffin et al. |
| 2002/0013540 | A1 | 1/2002 | Jacobsen et al. |
| 2002/0019599 | A1 | 2/2002 | Rooney et al. |
| 2002/0077594 | A1 | 6/2002 | Chien et al. |
| 2002/0082499 | A1 | 6/2002 | Jacobsen et al. |
| 2003/0009208 | A1 | 1/2003 | Snyder et al. |
| 2003/0060732 | A1 | 3/2003 | Jacobsen et al. |
| 2003/0069520 | A1 | 4/2003 | Skujins et al. |
| 2003/0069521 | A1 | 4/2003 | Reynolds et al. |
| 2003/0069522 | A1 | 4/2003 | Jacobsen et al. |
| 2003/0093059 | A1 | 5/2003 | Griffin et al. |
| 2003/0105415 | A1 | 6/2003 | Mirigian |
| 2003/0125709 | A1 | 7/2003 | Eidenschink |
| 2003/0130672 | A1 | 7/2003 | DoBrava et al. |
| 2004/0002713 | A1 | 1/2004 | Olson et al. |
| 2004/0111044 | A1 | 6/2004 | Davis et al. |
| 2004/0181174 | A2 | 9/2004 | Davis et al. |

FOREIGN PATENT DOCUMENTS

| | | | | |
|---|---|---|---|---|
| BR | 9712829-5 | A2 | 1/2000 | |
| CN | 1230914 | A | 9/2003 | |
| DE | 2539191 | A1 | 3/1976 | |
| EP | 0521595 | A2 | 1/1993 | |
| EP | 0608853 | A2 | 8/1994 | |
| EP | 0778038 | A2 | 6/1997 | |
| EP | 0778039 | A1 | 6/1997 | |
| EP | 0778040 | A2 | 6/1997 | |
| EP | 0790066 | A3 | 8/1997 | |
| EP | 0812599 | B1 | 12/1997 | |
| EP | 0835673 | A2 | 4/1998 | |
| EP | 0865773 | A1 | 9/1998 | |
| EP | 0917885 | A1 | 5/1999 | |
| EP | 0935947 | B1 | 8/1999 | |
| EP | 0937481 | A1 | 8/1999 | |
| JP | 63181774 | A | 7/1988 | |
| JP | 5507857 | A | 11/1993 | |
| JP | 6501179 | A | 2/1994 | |
| JP | 10305039 | A | 11/1998 | |
| JP | 10328191 | A | 12/1998 | |
| JP | 11226131 | A | 8/1999 | |
| JP | 11267224 | A | 10/1999 | |
| JP | 11276491 | A | 10/1999 | |
| JP | 2000510722 | A | 8/2000 | |
| JP | 2000511083 | A | 8/2000 | |
| JP | 2001500808 | A | 1/2001 | |
| JP | 2002529137 | A | 9/2002 | |
| JP | 2002542901 | A | 12/2002 | |
| JP | 2002543896 | A | 12/2002 | |
| JP | 2003517893 | A | 6/2003 | |
| WO | 9207619 | A1 | 5/1992 | |
| WO | 9304722 | A2 | 3/1993 | |
| WO | 9524236 | A1 | 9/1995 | |
| WO | 9619255 | A1 | 6/1996 | |
| WO | 9743949 | A1 | 11/1997 | |
| WO | 9744083 | A1 | 11/1997 | |
| WO | 9744086 | A1 | 11/1997 | |
| WO | WO 97/44086 | * | 11/1997 | ............ A61M 29/00 |
| WO | 9810694 | A2 | 3/1998 | |

(56) References Cited

FOREIGN PATENT DOCUMENTS

| | | |
|---|---|---|
| WO | 9839047 A1 | 9/1998 |
| WO | 9911313 A2 | 3/1999 |
| WO | 0027303 A1 | 5/2000 |
| WO | 0030710 A1 | 6/2000 |
| WO | 0048645 A1 | 8/2000 |
| WO | 0057943 A1 | 10/2000 |
| WO | 0066199 A1 | 11/2000 |
| WO | 0067845 A1 | 11/2000 |
| WO | 0069323 A2 | 11/2000 |
| WO | 0072907 A1 | 12/2000 |
| WO | 0128620 A1 | 4/2001 |
| WO | 0145773 A1 | 6/2001 |
| WO | 0193920 A2 | 12/2001 |
| WO | 0213682 A1 | 2/2002 |
| WO | 03004086 A2 | 1/2003 |

* cited by examiner

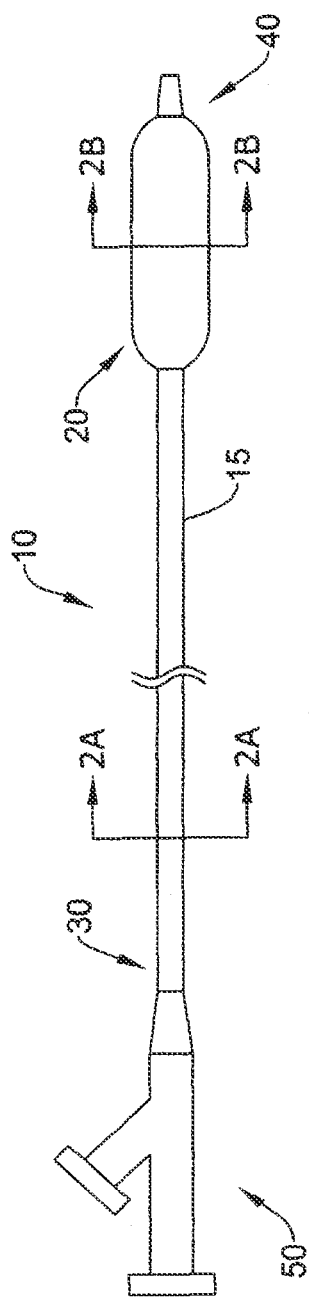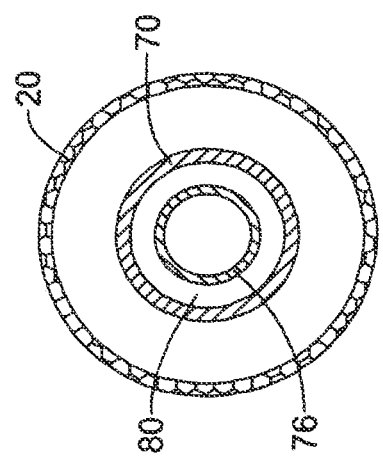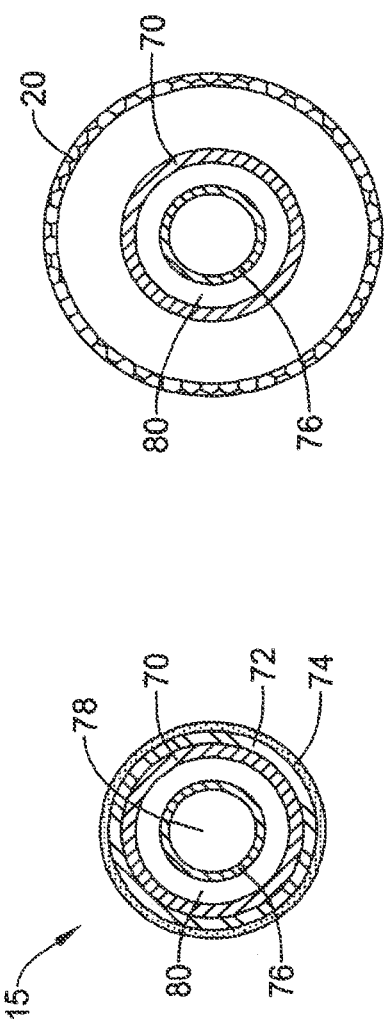
Figure 1
Figure 2A
Figure 2B

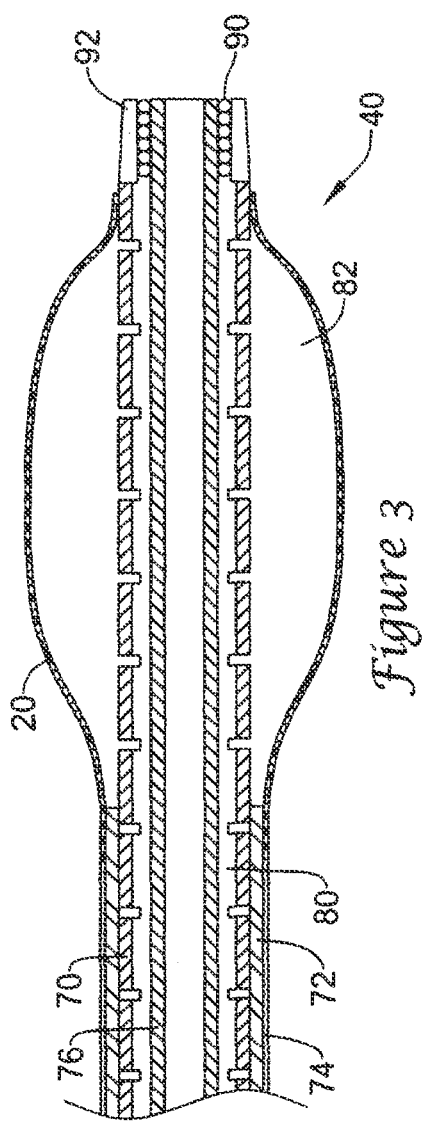
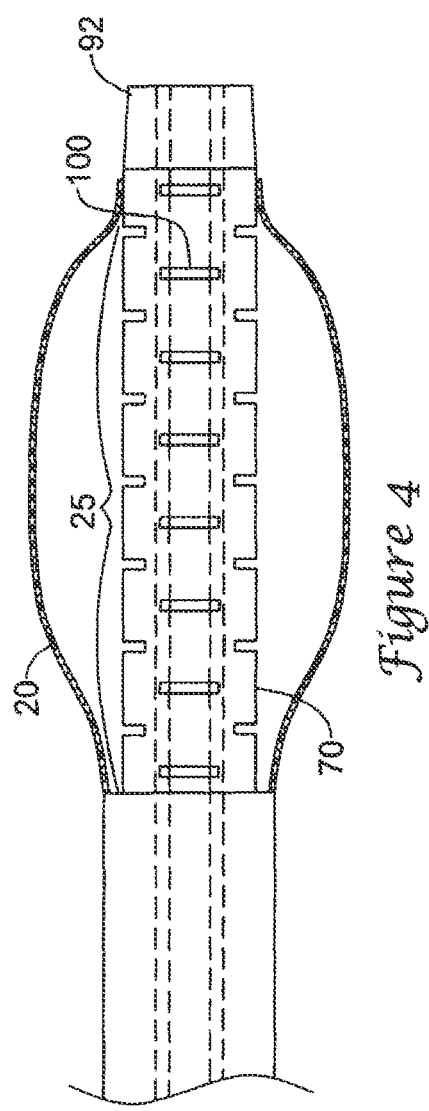

CATHETER INCLUDING A COMPLIANT BALLOON

RELATED APPLICATIONS

This application is a continuation of co-pending U.S. application Ser. No. 13/233,692, filed Sep. 11, 2013, which is a continuation of U.S. application Ser. No. 12/631,909, filed Dec. 7, 2009, now U.S. Pat. No. 8,021,329, which is a continuation of U.S. application Ser. No. 11/008,452, filed Dec. 9, 2004, now U.S. Pat. No. 7,632,242, the entire disclosures of which are hereby incorporated herein.

FIELD OF THE INVENTION

The present invention generally relates to medical devices for navigating body lumens. More specifically, the present invention relates to flexible medical devices for providing an inflatable balloon in a body lumen during a medical procedure.

BACKGROUND OF THE INVENTION

Medical devices such as intravascular and endovascular catheters are commonly used in medical procedures such as treatment of aneurysms, arteriovenous malformations (AVM), arteriovenous fistulae (AVF), as well as, intracranial procedures, neurological procedures, radiological procedures, and peripheral vascular procedures. There is an ongoing need to develop medical devices possessing improved characteristics in order to facilitate navigation of the tortuous vasculature of the human body during a medical procedure.

SUMMARY OF THE INVENTION

The present invention provides a medical device having improved characteristics for use during a medical procedure. The present invention includes an elongate shaft having a plurality of apertures formed along the length of the shaft to increase and/or control catheter flexibility and facilitate bending. An inflatable balloon may be placed at a distal portion of the elongate shaft and a hub assembly may be placed at a proximal portion of the elongate shaft. The hub assembly may include an inflation port in fluid communication with the inflatable balloon. There may be a polymer layer disposed along the portion of the shaft between the hub assembly and the inflatable balloon. The polymer layer covers the apertures along this portion to provide a fluid tight seal within the elongate shaft, while any apertures located on the portion of the elongate shaft including the hub assembly and the inflatable balloon remain unobstructed. Therefore, an inflation passageway is formed from the hub assembly, through the lumen of the elongate shaft, through the unobstructed apertures to the inflatable balloon.

BRIEF DESCRIPTION OF THE DRAWINGS

The invention may be more completely understood in consideration of the following detailed description of various embodiments of the invention in connection with the accompanying drawings, in which:

FIG. 1 is a plan view of a balloon catheter in accordance with an embodiment of the invention;

FIG. 2A is a cross-section taken along line 2A-2A in FIG. 1;

FIG. 2B is a cross-section taken along line 2B-2B in FIG. 1;

FIG. 3 is a cross-sectional view of the distal portion of a balloon catheter in accordance with an embodiment of the invention;

FIG. 4 is a partially sectioned view of the distal portion of a balloon catheter as embodied in FIG. 3;

DETAILED DESCRIPTION OF PREFERRED EMBODIMENTS

Figure 5:
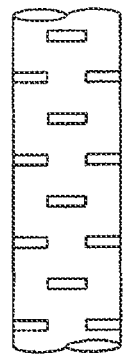
FIGS. 5-8 are alternate embodiments of a portion of the catheter in accordance with the invention.
Figure 6:
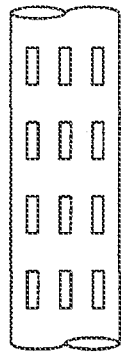
Figure 7:
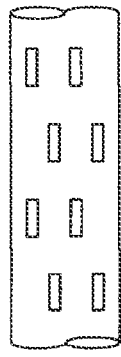
Figure 8:
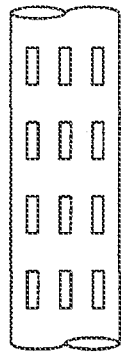

The following detailed description should be read with reference to the drawings in which similar elements in different drawings are numbered the same. The detailed description and the drawings, which are not necessarily to scale, depict illustrative embodiments and are not intended to limit the scope of the invention.

FIG. 1 generally shows a catheter 10 within the scope of the invention. In a preferred embodiment, the catheter 10 can include a distal portion 40 including an inflatable balloon 20 and a proximal portion 30 including a hub assembly 50. The catheter 10 can also include an elongate shaft 15 extending from the proximal portion 30 to the distal portion 40. The catheter 10 may have a length that is in the range of about 50 centimeters to about 250 centimeters.

FIG. 2A shows a cross-section of catheter 10 taken along line 2A-2A. As shown in FIG. 2A, the elongate shaft 10 may include an outer tubular member 70. The outer tubular member 70 may be formed of materials such as metals, metal alloys, polymers, metal-polymer composites, or other suitable materials. Some examples of some suitable materials may include stainless steels (e.g., 304v stainless steel), nickel-titanium alloys (e.g., nitinol, such as super elastic or linear elastic nitinol), nickel-chromium alloys, nickel-chromium-iron alloys, cobalt alloys, nickel, titanium, platinum, or alternatively, a polymer material such as a high performance polymer, or other suitable materials, and the like.

As can be better shown in FIGS. 5-8, outer tubular member 70 may include a plurality of apertures 100 formed along the length of outer tubular member 70 to increase the flexibility of the elongate shaft 15 to a desired level. Apertures 100 may be slots, slits, grooves, helical cuts, or the like. The spacing, depth and type of apertures 100 may be varied to control the flexure profile and torsional stiffness of the outer tubular member 70. The spacing of apertures 100 may vary gradually along outer tubular member 70, or may change incrementally. Apertures 100 may extend through the wall of the outer tubular member 70, or they may extend only partially through the wall. It is contemplated that at least some of the apertures extend through the wall of the outer tubular member 70. Apertures may be micromachined into the outer tubular member 70 by electrostatic discharge machining (EDM), chemical milling, ablation, laser cutting, saw cutting, grinding, etching, or the like. Apertures 100 may extend substantially the full length of the elongate shaft 15, or apertures may be positioned along selected portions of the elongate shaft 15 where increased flexibility is desired. Such techniques for creating apertures 100 along the outer tubular member 70 are discussed in detail in U.S. Patent Publication 2003/0069522 to Jacobsen et al., as herein incorporated by reference in its entirety.

A polymer layer 72 may be disposed about at least a portion of the outer tubular member 70. Polymer layer 72 may extend from the proximal portion 30 to the distal portion 40 of outer tubular member 70. The polymer layer may cover the apertures 100 along a portion of the outer tubular member 70, providing the outer tubular member 70 with a fluid tight seal along the portion having the polymer 72. Polymer layer 72 may be formed of a flexible material such as polyurethane, low-density polyethylene (LDPE), polyvinyl chloride, polyether block amide (PEBAX), styrene-ethylene/butylenes-styrene (SEBS), styrene-butadiene-styrene (SBS), as well as other polymers of suitable properties.

In some embodiments, part of or all of the elongate shaft 15 may be coated with a lubricious layer 74 such as a hydrophilic polymer such as polyarylene oxides, polyvinylpyrrolidones, polyvinylalcohols, hydroxyl alkyl cellulosics, aligns, saccharides, caprolactones, and the like, and mixtures and combinations thereof. Lubricious layer 74 may improve steerability and improve lesion crossing capability of the catheter 10. The lubricious layer 74 may be chemically bonded to polymer layer 72 or physically coated on the surface of polymer layer 72. In some embodiments, a distal portion of the catheter 10 may be coated with a hydrophilic polymer, while the more proximal portions may be coated with a fluoropolymer. Lubricious layer 74 may be absent from the elongate shaft, or a portion thereof.

As shown in FIG. 2A, an inner tubular member 76 may be disposed within the outer tubular member 70. The outer surface of the inner tubular member 76 is spaced away from the inner surface of the outer tubular member 70, defining an annular inflation lumen 80 therebetween. The inner tubular member 76 may extend substantially the entire length of the catheter 10. The inner tubular member may provide a lumen 78 for a guidewire or delivering a medical device.

The inner tubular member 76 may be formed of materials such as metals, metal alloys, polymers, metal-polymer composites, or other suitable materials. Some examples of some suitable materials may include high-density polyethylene (HDPE), low-density polyethylene (LDPE), silicon, fluoropolymer, liquid crystal polymer (LCP), polyimide, polyamide, polyester, polyethylene (PE), polypropylene, polyvinyl chloride (PVC), polyfluorocarbon, polyurethane, polysulfone, ethyl vinyl acetate (EVA), polyether block amide (PEBAX), styrene-ethylene/butylenes-styrene (SEBS), styrene-butadiene-styrene (SBS), polyethylene terephthalate (PET), and their mixtures, alloys, blends, copolymers, and block copolymers.

FIG. 2B shows a cross-section taken along line 2B-2B at distal portion 40 of catheter 10. Distal portion 40 includes inflatable balloon 20 disposed about elongate shaft 15. In one embodiment, the inflatable balloon 20 is a compliant inflatable membrane with elastomeric properties. Inflatable balloon 20 may be formed of a urethane polymer or a thermoplastic rubber elastomer, such as Chronoprene™, available from CardioTech International, Inc. The balloon 20 may be expandable between a collapsed configuration and an inflated configuration. Upon inflation, the balloon 20 may conform to the shape of the interior of a body lumen in which the catheter 10 is disposed, such as a blood vessel. In the collapsed configuration (not shown), the balloon 20 may be collapsed about the distal portion 20 of the catheter 10 to create a low profile. As can be seen in FIG. 2B, at least a portion of the outer tubular member 70 of the elongate shaft 15 proximate the inflatable balloon 20 is free of the polymer layer 72. As can more clearly be seen in FIG. 4, apertures 100 along the portion of the outer tubular member 70 including the balloon 20 are free of the polymer layer 72. Unobstructed apertures 100 may be a subset of the apertures 100 extending along the length of the outer tubular member 70. Unobstructed apertures 100 along distal balloon section 25 are preferably formed during the same process as forming apertures 100 along the length of the outer tubular member 70, as discussed above. Unobstructed apertures 100 in distal balloon section 25 allow for fluid communication between the interior of the balloon 82 and inflation lumen 80. Inflation of the balloon 20 will be described in more detail with regard to FIGS. 3 and 4.

FIGS. 3 and 4 show a distal portion 40 of the catheter 10. FIG. 3 shows a cross-sectional view of the distal portion 40, while FIG. 4 shows a plan view of distal portion 40 with inflatable balloon 20 shown in cross-section. The distal portion 40 of the catheter 10 includes a distal balloon section 25 free of the polymer layer 72. The distal balloon section 25 may extend substantially the length of the balloon 20 or a portion thereof. The distal balloon section 25 includes a subset of apertures 100 formed about outer tubular member 70. At least some of apertures 100 in distal balloon section 25 extend through the wall of outer tubular member 70. Unobstructed apertures 100 in the distal balloon section 25 provide fluid communication between the interior of the balloon 82 and inflation lumen 80. Further, it is noted that flexibility under the balloon can be dramatically increased by the combination of multiple apertures and lack of polymer coating, which would tend to reduce flexibility. Further, the multiple apertures allow for quick inflation/deflation of the balloon.

A distal tip 92 may be placed distal of the balloon 20. Inner tubular member 76 may extend into distal tip 92. Distal tip may include a coil 90 to provide flexibility during navigation of the tortuous vasculature. Distal tip 92 may occlude the distal end of inflation lumen 80 to provide a fluid-tight passageway along the length of elongate shaft 15 to inflatable balloon 20. Distal tip may include radiopaque material. Radiopaque materials are understood to be materials capable of producing a relatively bright image on a fluoroscopy screen or other imaging technique during a medical procedure. Some examples of radiopaque materials may include, but are not limited to, gold, platinum, palladium, tantalum, tungsten alloy, plastic material loaded with a radiopaque filler, and the like.

Figure 9:
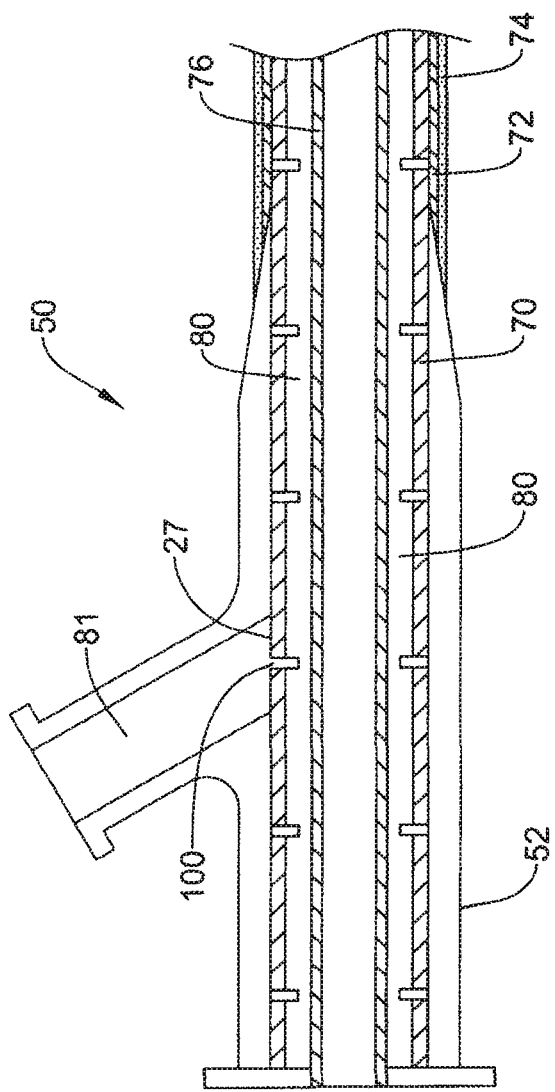
FIG. 9 is a cross-sectional view of the proximal portion of a catheter in accordance with an embodiment of the invention.

FIG. 9 shows one embodiment of the proximal portion 30 of the catheter 10. Proximal portion 30 includes a hub assembly 50. Hub assembly 50 includes hub 52 disposed about a portion of elongate shaft 15. Outer tubular member 70 extends into at least a portion of hub 50. Inner tubular member 76 may extend into at least a portion of hub 50 and may provide a working lumen 78 extending to the proximal end of hub 52 for use during a medical procedure. As shown in FIG. 9, polymer layer 72 may terminate distal of the hub assembly 50. Termination of polymer layer 72 distal of hub assembly 50 provides a proximal segment 27 of outer tubular member 70 free of the polymer layer 72. Proximal segment 27 may include a plurality of apertures 100 disposed along outer tubular member 70 unobstructed by the polymer layer 72. Unobstructed apertures 100 may be a subset of the apertures 100 extending along the length of the outer tubular member 70. Unobstructed apertures 100 along proximal segment 27 are preferably formed during the same process as forming apertures 100 along the length of the outer tubular member 70, as discussed above. At least some of apertures 100 disposed along proximal segment 27 extend through the wall of outer tubular member 70. The hub assembly 50 may also include an inflation port 81. Inflation port 81 may be disposed about at least a portion of the elongate shaft 15 including the proximal segment 27 having unobstructed apertures 100. Unobstructed apertures 100 in proximal segment 27 provide fluid communication between inflation port 81 and inflation lumen 80 of catheter 10.

Figure 10:
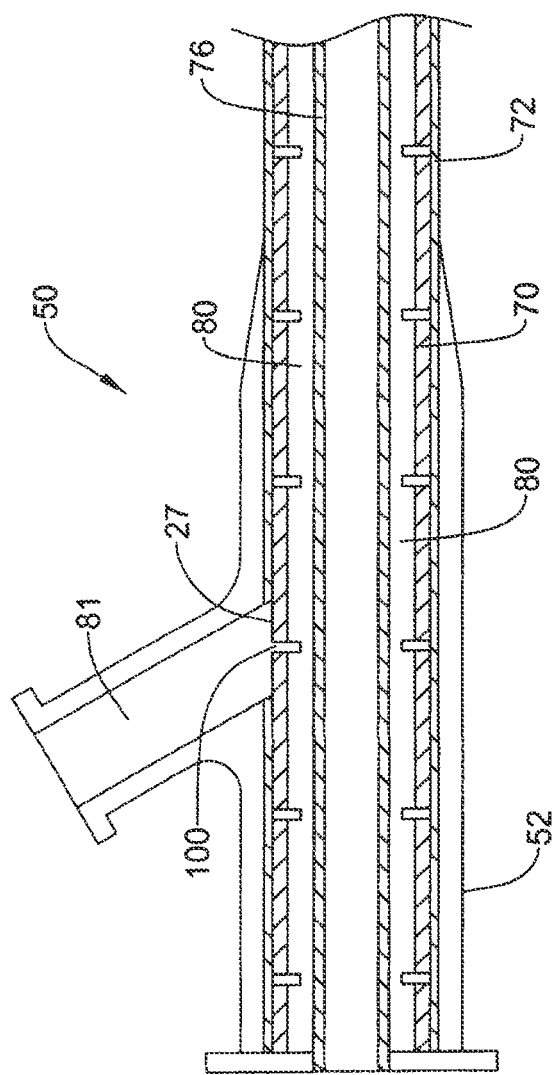
FIG. 10 is a cross-sectional view of the proximal portion of another catheter in accordance with an embodiment of the invention and FIG. 11 is a cross-sectional view of the proximal portion of another catheter in accordance with an embodiment of the invention.

FIG. 10 shows another embodiment of the proximal portion 30 of the catheter 10 in accordance with the invention. In this embodiment, polymer layer 72 extends into at least a portion of the hub assembly. However, proximal segment 27 adjacent to inflation port 81 is free of the polymer layer 72, such that a plurality of apertures 100 are unobstructed by the polymer layer 72 along proximal segment 27.

Figure 11:
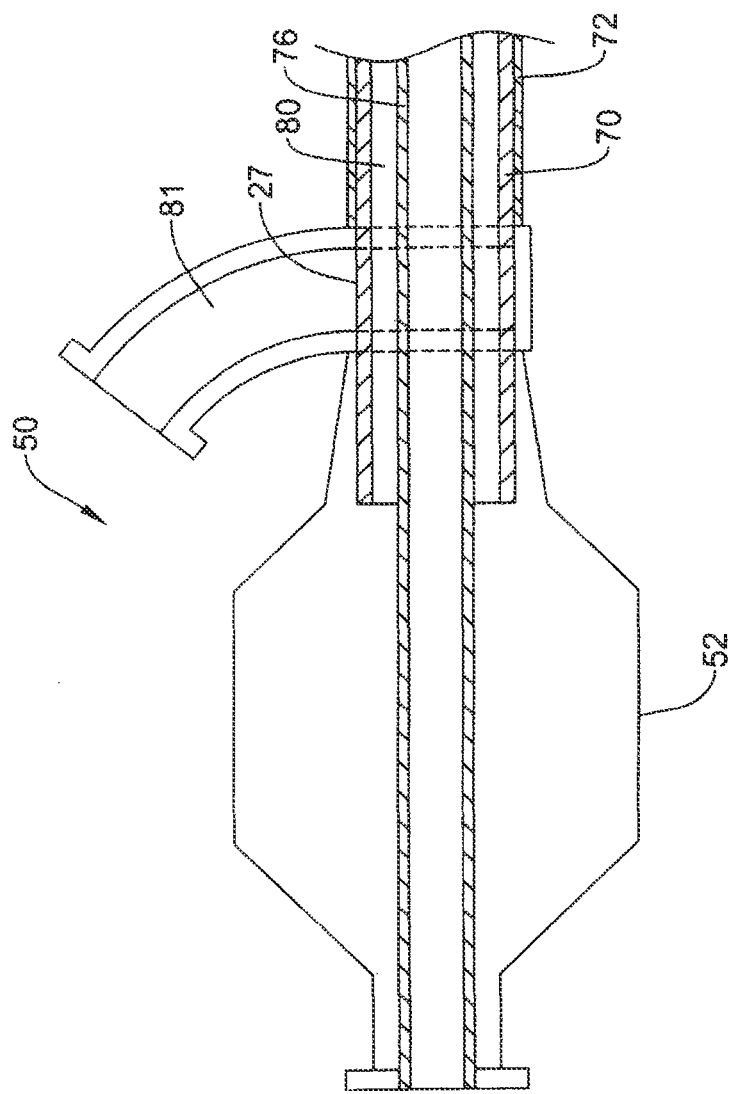

FIG. 11 shows another embodiment of the proximal portion 30 of the catheter 10 in accordance with the invention. Hub assembly 50 may include a hub 52 and an inflation port 81. Inflation port 81 is disposed about at least a portion of proximal segment 27 free of the polymer layer 72. Unobstructed apertures 100 provide fluid communication between inflation port 81 and inflation lumen 80. Inner tubular member 76 may extend substantially to distal end of the hub 50 to provide a working lumen 78.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What we claim is:

1. A balloon catheter, comprising:
   a first tubular member;
   a second tubular member disposed about the first tubular member, the second tubular member having a proximal region and a distal region;
   wherein one or more cuts are formed in the second tubular member;
   a coating disposed along at least the proximal region of the second tubular member;
   wherein the coating fluidly seals the one or more cuts along the proximal region of the second tubular member;
   a balloon coupled to the distal region of the second tubular member, wherein a portion of the distal region of the second tubular member extends inside the balloon and includes one or more cuts therein, wherein a proximal waist of the balloon extends over a distal region of the coating; and
   wherein an inflation lumen is defined between the first tubular member and the second tubular member.

2. The balloon catheter of claim 1, wherein the first tubular member, the second tubular member, or both include a nickel-titanium alloy.

3. The balloon catheter of claim 1, wherein the first tubular member, the second tubular member, or both include stainless steel.

4. The balloon catheter of claim 1, wherein the one or more cuts includes a helical cut.

5. The balloon catheter of claim 1, wherein the second tubular member has a tube wall and wherein at least some of the one or more cuts extend only partially through the tube wall.

6. The balloon catheter of claim 1, wherein the second tubular member has a tube wall and wherein the one or more cuts extend completely through the tube wall.

7. The balloon catheter of claim 1, wherein the one or more cuts extend along the full length of the second tubular member.

8. The balloon catheter of claim 1, wherein the one or more cuts extend along only a portion of the length of the second tubular member.

9. The balloon catheter of claim 1, wherein the distal region of the second tubular member inside the balloon is free of the coating.

10. The balloon catheter of claim 1, wherein the distal region of the second tubular member is free of an outer coating such that the one or more cuts along the distal region of the second tubular member are unobstructed so that fluid can pass between the inflation lumen and the balloon.

11. A balloon catheter, comprising:
    an inner tubular member defining a guidewire lumen;
    an outer tubular member disposed about at least a portion of the inner tubular member;
    wherein the outer tubular member has one or more slots formed therein;
    wherein the outer tubular member has a coated region and at least one uncoated region;
    a balloon coupled to the outer tubular member, wherein a portion of the outer tubular member extends inside the balloon and includes one of the uncoated regions; and
    wherein at least a section of the balloon is disposed along the uncoated region, wherein a proximal waist of the balloon extends over a portion of the coated region.

12. The balloon catheter of claim 11, wherein a distal tip is coupled to the inner tubular member, the outer tubular member, or both.

13. The balloon catheter of claim 12, wherein an inflation lumen is defined between the inner tubular member and the outer tubular member, and wherein at least a portion of the distal tip occludes a distal end of the inflation lumen.

14. The balloon catheter of claim 13, wherein a coil member is disposed along a length of the inner tubular member adjacent to the distal tip.

15. The balloon catheter of claim 11, wherein the one or more slots includes a single helical slot.

16. The balloon catheter of claim 11, wherein the outer tubular member has a tube wall and wherein at least some of the one or more slots extend only partially through the tube wall.

17. The balloon catheter of claim 11, wherein the outer tubular member has a tube wall and wherein the one or more slots extend completely through the tube wall.

18. The balloon catheter of claim 11, wherein the one or more slots extend along the full length of the outer tubular member.

19. The balloon catheter of claim 11, wherein the one or more slots extend along only a portion of the length of the outer tubular member.

20. A medical device, comprising:
    a tube having a proximal region, a middle region, a distal region, a length extending between the proximal and distal regions, the tube defining a lumen;
    wherein a single helical cut is formed in the tube, the single helical cut extending along the entire length of the tube;
    a coating disposed along the middle region of the tube;
    wherein the coating fluidly seals the helical cut along the proximal region of the tube;

an inner tubular member disposed within the lumen of the tube, wherein the inner tubular member is separated from the tube by a space, and wherein the space between the tube and the inner tubular member defines an inflation lumen; and wherein the distal and proximal regions of the tube are free of the coating such that fluid can move between the inflation lumen and an exterior surface of the tube.

\* \* \* \* \*